United States Patent [19]

Schor et al.

[11] 4,369,172

[45] Jan. 18, 1983

[54] PROLONGED RELEASE THERAPEUTIC COMPOSITIONS BASED ON HYDROXYPROPYLMETHYLCELLULOSE

[75] Inventors: Joseph M. Schor, Locust Valley; Ashok Nigalaye, Elmhurst, both of N.Y.; Norman G. Gaylord, New Providence, N.J.

[73] Assignee: Forest Laboratories Inc., New York, N.Y.

[21] Appl. No.: 332,348

[22] Filed: Dec. 18, 1981

[51] Int. Cl.$^3$ .......................... A61K 9/02; A61K 9/20; A61K 9/22; A61K 9/26

[52] U.S. Cl. .......................................... 424/19; 424/22; 424/362

[58] Field of Search .................................. 424/19–22, 424/362

[56] References Cited

U.S. PATENT DOCUMENTS

| | | | |
|---|---|---|---|
| 2,887,440 | 5/1959 | Greminger et al. | 424/362 |
| 3,065,143 | 11/1962 | Christenson et al. | 424/19 |
| 3,839,319 | 10/1974 | Greminger et al. | 424/362 |
| 3,852,421 | 12/1974 | Koyanagi et al. | 424/362 |
| 3,870,790 | 3/1975 | Lowey et al. | 424/19 |
| 4,091,205 | 5/1978 | Onda et al. | 424/362 |
| 4,167,558 | 9/1979 | Sheth et al. | 424/19 |
| 4,226,849 | 10/1980 | Schor | 424/19 |
| 4,259,314 | 3/1981 | Lowey | 424/19 |
| 4,265,875 | 5/1981 | Byrne et al. | 424/362 |
| 4,292,299 | 9/1981 | Suzuki et al. | 424/19 |

*Primary Examiner*—Shep K. Rose
*Attorney, Agent, or Firm*—Jacobs & Jacobs

[57] ABSTRACT

A carrier base material combined with a therapeutically active medicament and shaped and compressed to a solid unit dosage form having a regular and prolonged release pattern upon administration, the carrier base material being hydroxypropylmethylcellulose or a mixture of hydroxypropylmethylcellulose and up to 30% by weight of the mixture of ethylcellulose and/or up to 30% by weight of the mixture of sodium carboxymethylcellulose, and wherein the hydroxypropylmethylcellulose has a hydroxypropoxyl content of 9–12 weight % and a number average molecular weight of less than 50,000.

38 Claims, No Drawings

PROLONGED RELEASE THERAPEUTIC COMPOSITIONS BASED ON HYDROXYPROPYLMETHYLCELLULOSE

BACKGROUND OF THE INVENTION

1. Field of Invention

This invention relates to a carrier base material to be combined with a therapeutically active medicament and formed into a solid shaped dosage unit having a long-lasting and regular incremental release of the medicament upon administration. Specifically, this invention relates to a carrier base material, consisting essentially or predominantly of hydroxypropylmethylcellulose having a chemical structure and molecular weight which renders it suitable for use in prolonged release therapeutic compositions.

2. Description of the Prior Art

Hydroxypropylmethylcelluloses are commercially available in various grades, under several tradenames, including Methocel E, F, J and K (all previously designated as Methocel HG) from The Dow Chemical Co., U.S.A., HPM from British Celanese, Ltd., England, and Metalose SH from Shin-Etsu, Ltd., Japan. The various grades available under a given tradename represent differences in methoxy and hydroxypropoxyl content as well as molecular weight. The methoxyl content ranges from 16.5 to 30 weight-% and the hydroxypropoxyl content ranges from 4 to 32 weight-%, as determined by the method described in ASTM D-2363-72.

Commercial designations of the various hydroxypropylmethylcelluloses are based on the viscosities of 2% aqueous solutions at 20° C. The viscosities range from 15 cps to 30,000 cps and represent number average molecular weights (Mn) ranging from about 10,000 to over 150,000.

Christenson and Dale (U.S. Pat. No. 3,065,143) disclosed the use of certain hydrophilic gums, including hydroxypropylmethylcelluloses, in the preparation of a "sustained release tablet". The tablet consisted essentially of a mixture of a medicament and at least one third part by weight of the weight of the tablet of a hydrophilic gum which rapidly absorbed water and swelled at 37° C. to form a "soft mucilaginous gel barrier" on the surface of the tablet when brought into contact with the aqueous fluids of the gastro-intestinal tract.

The ability to form a "soft mucilaginous gel" on contact with aqueous fluids is dependent upon the molecular weight of the hydrophilic gum including hydroxypropylmethylcelluloses. The need to use high molecular weight polymers is evident from the disclosures of those which are effective in the practice of the invention of U.S. Pat. No. 3,065,143. Thus, Examples 1 and 7 disclose the use of Methocel 60HG 4000 cps, Example 4 discloses the use of Methocel 90HG 4000 cps, and Example 5 discloses the use of Methocel 90HG 15,000 cps.

Methocel 60HG 4000 cps, now known as Methocel E4M, has a 28-30 weight-% methoxyl content and a 7.5-12 weight-% hydroxypropoxyl content. The 4000 cps viscosity grade indicates that the polymer has a number average molecular weight of 93,000, as calculated from the data in "Handbook of Methocel Cellulose Ether Products" (The Dow Chemical Co., 1974).

Methocel 90HG 4000 cps and Methocel 90HG 15,000 cps, now known as Methocel K4M and Methocel K15M, respectively, have a 19-24 weight-% methoxyl content and a 4-12 weight-% hydroxypropoxyl content. The 4000 cps and 15,000 cps viscosities indicate that the polymers have number average molecular weights of 89,000 and 124,000, respectively.

The other examples in U.S. Pat. No. 3,065,143 disclose the use of "extra high viscosity" sodium carboxymethylcellulose and carboxypolymethylene, both having high molecular weights, as effective hydrophilic gums. In contrast, Example 1 discloses that 400 cps methylcellulose is ineffective in the practice of the invention. This polymer has a number average molecular weight of 41,000 ("Handbook of Methocel Cellulose Ether Products", loc. cit.).

Christenson and Huber (U.S. Pat. No. 3,590,117) reported that high viscosity, i.e. 15,000 cps, hydroxypropylmethylcellulose did not make an acceptable long-lasting troche because the troche would flake off in the mouth rather than dissolve uniformly. "Low viscosity" hydroxypropylmethylcellulose yielded unacceptable troches because they generated extremely viscous and adhesive saliva which resulted in a gagging response (column 1, lines 29-47).

The use of modified lower molecular weight hydroxypropylmethylcellulose, per se and in admixture with either ethylcellulose or sodium carboxymethylcellulose, as a carrier base in sustained release pharmaceutical compositions is disclosed by Lowey and Stafford (U.S. Pat. No. 3,870,790) and Schor (U.S. Pat. No. 4,226,849). The Methocel E50 disclosed in these patents was formerly known as Methocel 60HG 50 cps and has a number average molecular weight of 23,000. However, the polymer is modified for use in sustained release solid dosage units by exposure to high humidity or moisture and drying in a current of air.

The present invention is directed toward further improvements in carrier bases containing hydroxypropylmethylcelluloses for use in the preparation of solid pharmaceutical unit dosages which have sustained release.

SUMMARY OF THE INVENTION

An object of the present invention is to provide a carrier material for use in the preparation of orally, bucally or sublingually, etc., administered lozenges and tablets, as well as suppositories and other solid unit dosage forms which have a regular and prolonged release pattern for a systemically absorbable medicament or active ingredient incorporated therein.

Another object of the present invention is to provide a carrier base having greater stability, greater hardness, lower friability, reduced water solubility and a more prolonged release pattern from hydroxypropylmethylcellulose.

It has now been found that these improvements in a carrier base can be achieved by utilizing a low viscosity grade hydroxypropylmethylcellulose having a number average molecular weight below 50,000 and a hydroxypropoxyl content of 9-12 weight-%.

DETAILED DESCRIPTION OF THE INVENTION

According to the present invention, it has now been found that important advantages and improvements over prior products containing hydroxypropylmethylcelluloses, as described in U.S. Pat. Nos. 3,065,143, 3,870,790 and 4,226,849, can be obtained by utilizing a low viscosity grade hydroxypropylmethylcellulose having a hydroxypropoxyl content of 9-12 weight-%.

The hydroxypropylmethylcellulose used in the present invention has a methoxyl content of 27-30 weight-%, a hydroxypropoxyl content of 9-12 weight-% and a number average molecular weight of less than 50,000.

The methoxyl contents of both Methocel E, commercially available from the Dow Chemical Co., U.S.A., and Metalose 60SH, commercially available from Shin-Etsu Ltd., Japan, are reported to range, typically, from 28-30 weight-%. The hydroxypropoxyl content of Methocel E is reported to range, typically, from 7.5 to 12 weight-%, while that of Metalose 60SH is reported to range, typically, from 7 to 12 weight-%. The methoxyl and hydroxypropoxyl contents are determined by the test procedures described in ASTM D2363-72.

Surprisingly, actual analyses of numerous lots of the commercially available materials revealed that, in contrast to the broad range of the reported typical analyses, the actual hydroxypropoxyl content of Methocel E50 was consistently below 9 weight-% while that of Metalose 60SH50 was consistently above 9 weight-%.

U.S. Pat. No. 3,065,143 discloses that a 4000 cps grade of hydroxypropylmethylcellulose having a number average molecular weight of 93,000, e.g. Methocel E4M, is effective in the preparation of a sustained release tablet containing an active medicament by virtue of its ability to form a soft, mucilaginous gel barrier on the surface of the tablet when brought into contact with aqueous fluids and when it constitutes at least one-third of the total weight of the tablet.

We have found that a similar tablet prepared from a 50 cps grade of hydroxypropylmethylcellulose, having a number average molecular weight of 23,000, e.g. Methocel E50 and Metalose 60SH50, behaves in an entirely different manner on contact with water and forms little or no soft mucilaginous gel barrier.

When samples of this low viscosity grade hydroxypropylmethylcellulose, having a hydroxypropoxyl content below 9 weight-%, are humidified and air dried, in accordance with the processes disclosed in U.S. Pat. Nos. 3,870,790 and 4,226,849, then mixed with an active medicament and tableted, the resultant tablets provide sustained release of the medicament despite the failure to form the soft mucilaginous gel which is obtained when the higher molecular weight hydroxypropylmethylcellulose is used.

Although the low viscosity grade hydroxypropylmethylcellulose having a hydroxypropoxyl content below 9 weight-% may be used, without prior treatment, i.e. without humidification and air drying, in the preparation of a tablet providing sustained release of the medicament, the mixture with the untreated polymer has poor compressibility and the tablet prepared therefrom is softer, flakier and more friable than the tablet prepared from the treated polymer.

Surprisingly, when samples of the low viscosity grade hydroxypropylmethylcellulose having a hydroxypropoxyl content of 9-12 weight-% are mixed, without prior treatment, with an ctive medicament, the mixture has excellent compressibility and the tablets prepared therefrom are hard and dense and the friability is significantly lower than that of tablets prepared with treated or untreated hydroxypropylmethylcellulose having a hydroxypropoxyl content of less than 9 weight-%. The tablets from the low viscosity grade hydroxypropylmethylcellulose having a hydroxypropoxyl content above 9 weight-% also provide a slower release rate of the active medicament, i.e. they provide sustained release over a somewhat longer period.

In contrast to the improved results obtained when polymer having less than 9 weight-% hydroxypropoxyl content is treated by humidification and air drying before conversion to sustained release tablets, similar treatment of the polymer having a hydroxypropoxyl content above 9 weight-% has little or no effect on the compressibility of the polymer and the properties of the tablets prepared therefrom.

The preparation of phasal tablets containing lithium carbonate, using hydroxypropylmethylcelluloses having hydroxypropoxyl contents both below and above 9 weight-%, each with and without prior humidification and drying, is described in Examples 1-4.

EXAMPLES 1-4

Anti-Manic Depressive

Phasal tablets containing lithium carbonate were prepared from the following ingredients:

| | Ingredients | grams | mg/tablet |
|---|---|---|---|
| 1 | Lithium carbonate | 150 | 300 |
| 2 | Hydroxypropylmethylcellulose | 200 | 400 |
| 3 | Cherry flavor | 0.6 | 1.2 |
| 4 | Magnesium stearate | 0.4 | 0.8 |

Hydroxypropylmethylcelluloses, i.e. Methocel E50 and Metalose 60SH50, having different hydroxypropoxyl contents (HP) were used in the preparation of the phasal tablets, with and without prior humidification and drying. The following polymers were used:

| No. | Polymer | HP, weight % | Treatment |
|---|---|---|---|
| A | Methocel E50 | 8.0 | None |
| B | Methocel E50 | 8.0 | Yes |
| C | Metalose 60SH50 | 10.3 | None |
| D | Metalose 60SH50 | 10.3 | Yes |

Ingredients 1 and 2 were mixed and blended in a bowl, ingredient 3 was added and, after mixing, was followed by ingredient 4. The mixture was blended for 20 minutes and then subjected to compression in a tableting machine having a 0.5 inch die and a 0.5 inch punch under a compression pressure of 10 kg/sq. in. to make 500 tablets with an average weight of 700 mg and a thickness of 0.185-0.205 inches.

The tablets had a moisture content of 4.5-5.5% and had the following properties:

| Example No. | 1 | 2 | 3 | 4 |
|---|---|---|---|---|
| Polymer | A | B | C | D |
| HP, weight % | 8.0 | 8.0 | 10.3 | 10.3 |
| Treatment | None | Yes | None | Yes |
| Hardness, kg | 4.0 | 5.0 | 8.5 | 8.5 |
| Friability, % | 2.4 | 1.0 | 0.4 | 0.5 |
| Release rate, % | | | | |
| 1st hour | 23.2 | 20.6 | 18.1 | 19.3 |
| 4th hour | 54.0 | 65.8 | 52.3 | 47.3 |
| 7th hour | 95.3 | 96.1 | 75.8 | 76.1 |
| 8th hour | 100 | — | 81.0 | 83.6 |
| 14th hour | — | — | 95.1 | 100 |
| 16th hour | — | — | 99.4 | — |

The hardness of the tablets was determined on a Pennwalt Stokes hardness tester. The friability was determined in a Erweka Friabilator (Erweka- Apparatebau GmbH, Heuenstamm Kr. Offenbach-/Main, West Germany) by measuring the weight loss after 3 minutes rotation. The release rate was determined by using the release rate apparatus as described in NF XIV, page 985. Five tablets were placed into a 100 ml screw cap dissolution vial and 60 ml of a buffered solution of the desired pH, preheated to 37° C., was added to the vial. The vial was closed and rotated in the NF time release apparatus maintained at 40±2 rpm. At intervals of one hour, the vial was opened and the supernatant liquid was poured through a screen and collected. The collected liquid was quantitatively transferred to a 100 ml volumetric flask. The tablets on the screen and the vial were washed with deionized water, the washings being added to the flask. The washed tablets were returned to the vial from the screen with the aid of the next buffered solution and the closed vial was rotated in the bath for the next interval of one hour. The following schedule of buffered solutions was used:

| Hours | pH  | Hours | pH  |
|-------|-----|-------|-----|
| 1     | 1.2 | 9     | 7.5 |
| 2     | 2.5 | 10    | 7.5 |
| 3     | 4.5 | 11    | 7.5 |
| 4     | 7.0 | 12    | 7.5 |
| 5     | 7.0 | 13    | 7.5 |
| 6     | 7.5 | 14    | 7.5 |
| 7     | 7.5 | 15    | 7.5 |
| 8     | 7.5 | 16    | 7.5 |

The solutions separated from the tablets were analyzed for the concentration of lithium carbonate released from the tablet. The procedure was continued until at least 90% of the tablet had dissolved and/or essentially all of the medicament had been released.

The hydroxypropylmethylcellulose having a hydroxypropoxyl content of 9-12 weight-% can be optionally mixed with about 0 to 30% by weight of the mixture of ethylcellulose and/or about 0 to 30% of sodium carboxymethylcellulose. Thus, the hydroxypropylmethylcellulose content of the carrier base can range from 40 to 100%.

The active ingredient can be of any type of medication which acts locally in the mouth or systemically which in the case of the latter can be administered orally to transmit the active medicament into the gastrointestinal tract and into the blood, fluids and tissues of the body without excessive peak concentrations occurring. Alternatively, the active ingredient can be of any type of medication which acts through the buccal tissues of the mouth to transmit the active ingredient directly into the blood stream thus avoiding first pass liver metabolism and by-passing the gastric and intestinal fluids which often have an adverse inactivating or destructive action on many active ingredients unless they are specially protected against such fluids as by means of an enteric coating or the like. The active ingredient can also be of a type of medication which can be transmitted into the blood circulation through the rectal tissues.

Representative active medicaments include antacids, anti-inflammatory substances, coronary dilators, cerebral dilators, peripheral vasodilators, anti-infectives, psychotropics, antimanics, stimulants, antihistamines, laxatives, decongestants, vitamins, gastro-intestinal sedatives, antidiarrheal preparations, anti-anginal drugs, vasodilators, antiarrythmics, anti-hypertensive drugs, vasoconstrictors and migraine treatments, anticoagulants and antithrombotic drugs, analgesics, anti-pyretics, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs, and drugs or substances acting locally in the mouth.

Typical active medicaments include gastrointestinal sedatives such as metoclopramide and propantheline bromide, antacids such as aluminum trisilicate, aluminum hydroxide and cimetidine, anti-inflammatory drugs such as phenylbutazone, indomethacin, naproxen, ibuprofen, flurbiprofen, diclofenac, dexamethasone, prednisone and prednisolone, coronary vasodilator drugs such as glyceryl trinitrate, isosorbide dinitrate and pentaerythritol tetranitrate, peripheral and cerebral vasodilators such as soloctidilum, vincamine, naftidrofuryl oxalate, co-dergocrine mesylate, cyclandelate, papaverine and nicotinic acid, anti-infective substances such as erythromycin stearate, cephalexin, nalidixic acid, tetracycline hydrochloride, ampicillin, flucolaxacillin sodium, hexamine mandelate and hexamine hippurate, neuroleptic drugs such as fluazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine, central nervous stimulants such as methylphenidate, ephedrine, epinephrine, isoproterenol, amphetamine sulfate and amphetamine hydrochloride, anti-histamic drugs such as diphenhydramine, diphenylpyraline, chlorpheniramine and brompheniramine, anti-diarrheal drugs such as bisacodyl and magnesium hydroxide, the laxative drug, dioctyl sodium sulfosuccinate, nutritional supplements such as ascorbic acid, alph tocopherol, thiamine and pyridoxine, anti-spasmotic drugs such as dicyclomine and diphenoxylate, drugs effecting the rhythm of the heart such as verapamil, nifedepine, diltiazem, procainamide, disopyramide, bretylium tosylate, quinidine sulfate and quinidine gluconate, drugs used in the treatment of hypertension such as propranolol hydrochloride, guanethidine monosulphate, methyldopa, oxprenolol hydrochloride, captopril and hydralazine, drug used in the treatment of migraine such as ergotamine, drugs effecting coagulability of blood such as epsilon aminocaproic acid and protamine sulfate, analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid, anti-epileptic drugs such as phenytoin sodium and sodium valproate, neuromuscular drug such as dantrolene sodium, substances used in the treatment of diabetes such as tolbutamide, diabenase glucagon and insulin, drugs used in the treatment of thyroid gland disfunction such as triiodothyronine, thyroxine and propylthiouracil, diuretic drugs such as furosemide, chlorthalidone, hydrochlorthiazide, spironolactone and triampterene, the uterine relaxant drug ritodrine, appetite suppressants such as fenfluramine hydrochloride, phentermine and diethylproprion hydrochloride, anti-asthmatic drugs such as aminophylline, theophylline, salbutamol, orciprenaline sulphate and terbutaline sulphate, expectorant drug such as guaiphenesin, cough suppressants such as dextromethorphan and noscapine, mucolytic drugs such as carbocisteine, anti-septics such as cetylpyridinium chloride, tyrothricin and chlorhexidine, decongestant drugs such as phenylpropanolamine and pseudoephedrine, hypnotic drugs such as dichloralphenazone and nitrazepam, anti-nauseant drug such as promethazine theoclate, haemopoetic drugs such as ferrous sulphate, folic acid and calcium gluconate, uricosuric drugs such as sulphinpyrazone, allopurinol and probenecid and the like. However, it is to be understood that the invention is applicable to sublingual lozenges, buccal tablets, oral lozenges, suppositories and compressed tablets, the latter being intended to be swallowed in unit dosage form and which upon ingestion according to a prescribed regimen give slow and regular release of active medicaments without an initial dumping of a fixed percentage in the intestinal tract. It is further understood that the invention is not restricted to the above medications exampled.

The hydroxypropylmethylcellulose having a hydroxypropxyl content of 9–12 weight-% and a number average molecular weight of less than 50,000, alone or in admixture with ethylcellulose and/or sodium carboxymethylcellulose, forms what is called a long-acting, slow dissolving carrier of such nature that it has a protective, demulcent and buffering effect in the body and causes the active medicament to exert its optimum therapeutic action incrementally for many hours, so that full therapeutic advantage can be taken of the entire or substantially the entire amount of active medicament administered. This high degree of efficiency is a particular advantage of the invention.

In making up tablets containing an orally administrable systemically absorbable active component such as one of the heretofore mentioned medicaments, the oral carrier material is thoroughly intermixed with the medicament which is also in powdered or granular form or in solution, and any other needed ingredients which are conventional in tablet making such as magnesium stearate, lactose, starch and, in general, binders, fillers, disintegrating agents, and the like. The complete mixture, in an amount sufficient to make a uniform batch of tablets, e.g. 50,000, of which each contains an effective amount of active medicament, is then subjected to tableting in conventional tableting machines at compression pressures of 4 to 15 kg/sq. in. and because of the use of the specific carrier material of this invention in the production of the tablets, a product is obtained which has the desired hardness, low level of friability and a predetermined prolonged action and a regular delayed release pattern so that the medicament is available over a period of 1–24 hours, depending on the precise tablet size, hardness and the particular carrier composition. In this way, it is possible to produce sustained or slow continuous release tablets in relatively simple and economical manner on a commercial scale as contrasted with the more elaborate and more complex materials and procedures heretofore employed or proposed.

The moisture content of the carrier used in the preparation of the sustained release tablets may be in the 0.1–10% range, preferably 1–10%. If the moisture content is outside of this range, it may be brought within the range by the use of ambient or hot, dry or wet air, using appropriate equipment including static, convection, forced air or vacuum chambers or other equipment well known to those skilled in the art. The moisture content of the carrier during tableting influences the integrity of the tablet obtained under a given compression pressure. Thus, a moisture content above 5% permits the use of lower pressures while lower moisture contents require the use of higher pressures to obtain tablets of equivalent integrity.

The moisture content of the tablet consisting of the hydroxypropylmethylcellulose having a hydroxypropoxyl content of 9–12 weight-% and a number average molecular weight of below 50,000, the medicament and other ingredients, if any, has little or no influence on the sustained release characteristics and plays a minor role as compared to the chemical structure of the carrier on the rate of release of medicaments. Similarly, while the release pattern is governed at least in part by the size of the tablet or other shaped object as well as by the degree of compression, the chemical structure of the hydroxypropylmethylcellulose superimposes its effect and is the dominant factor in the control of the release rate.

Since the sustained release of medicaments resulting from the use of the carrier base of the present invention, having a number average molecular weight of less than 50,000, is due to the chemical structure of the carrier, rather than to the formation of a soft mucilaginous gel barrier on the surface of the tablet when a high molecular weight carrier, present to the extent of at least 33.3% of the total weight of the tablet, is brought into contact with aqueous fluids, as disclosed in U.S. Pat. No. 3,065,143, the amount of carrier base in the tablet may be as low as 2% of the total weight of the tablet. The amount of carrier base in the tablet directly influences the rate and duration of the release of the medicament and may range from 0.5 to 99.9 of the total weight of the tablet.

The release pattern of active medicament from the carrier of the present invention can be controlled according to the particular medication and its intended therapeutic effect. For a sublingual oral or buccal lozenge or tablet, the release pattern may be varied from about 15 minutes to 12 hours. For orally administered tablets, the rate of release may be 4–8 hours, 8–10 hours, 10–12 hours, etc., as desired. For vaginal and rectal suppositories, the release pattern ranges from 3 to 36 hours, and can be less where indicated. Predetermined release patterns of unusually reliable and constant characteristics can be secured. This is often very important medically, especially when treating patients having coronary diseases, such as angina pectoris with nitroglycerine, or related problems of circulatory disorders or abnormal blood pressure conditions or psychotropic/manic depressive schizophrenia. The invention is particularly important also in treating such conditions as ulcerated tissue or mucous lesions and other conditions which arise from local hyperacidity or metabolic dysfunction in the physiological system. The invention is therefore of very versatile and adaptable nature giving it a wide range of application and end use.

Examples 5 and 6 describe the use of untreated hydroxypropylmethylcelluloses having hydroxypropoxyl contents both below and above 9 weight-%, in the preparation of aspirin tablets where the carrier base constitutes only 16.5% of the total weight of the tablet.

EXAMPLES 5-6

Aspirin

Aspirin tablets containing 650 mg/tablet were prepared from the following ingredients:

|   | Ingredients | grams | mg/tablet |
|---|---|---|---|
| 1 | Aspirin, crystalline | 650 | 650 |
| 2 | Hydroxypropylmethylcellulose | 130 | 130 |
| 3 | Lubritab | 7 | 7 |

Hydroxypropylmethylcelluloses, i.e. Methocel E50 and Metalose 60SH50, having different hydroxypropoxyl contents (HP), were used in the preparation of the aspirin tablets, without prior treatment.

Ingredients 1 and 2 were mixed in a PK blender for 20 minutes, ingredient 3 was added to the blend and mixing was continued for an additional 10 minutes. The mixture was used to prepare 1000 tablets on the Stokes B2 tablet machine using 0.281 inch×0.625 inch capsule shape dies and punches at a compressive pressure of 10 kg/sq. in. The average weight of the tablets was 787 mg and the thickness was 0.280-0.285 inches.

The hardness, friability and release rate of the tablets were determined as described earlier, to give the following results:

| Example No. | 5 | 6 |
|---|---|---|
| Polymer | Methocel E50 | Metalose 60SH50 |
| HP, weight % | 8.0 | 10.3 |
| Treatment | none | none |
| Hardness, kg | 6.0 | 8.2 |
| Friability, % | 0.5 | 0.3 |
| Release rate, % | | |
| 1st hour | 94.0 | 15.7 |
| 2nd hour | 100 | 26.5 |
| 4th hour | — | 49.4 |
| 6th hour | — | 77.0 |
| 8th hour | — | 100 |

It is apparent that the untreated hydroxypropylmethylcellulose having a hydroxypropoxyl content above 9 weight-%, even in low concentrations, yields tablets with good compressibility, as indicated by the hardness and friability, while providing for sustained release of the medicament.

EXAMPLE 7

Vitamin

Ascorbic acid tablets containing 500 mg/tablet were prepared from untreated Metalose 60SH50 hydroxypropylmethylcellulose having a 10 wt-% hydroxypropoxyl content and the following ingredients:

|   | Ingredients | grams | mg/tablet |
|---|---|---|---|
| 1 | Ascorbic acid | 250 | 500 |
| 2 | Hydroxypropylmethylcellulose (10 wt % HP) | 50 | 100 |
| 3 | Magnesium stearate | 0.5 | 1 |
| 4 | Stearic acid | 3 | 6 |

Ingredients 1 and 2 were mixed for 15 minutes, ingredients 3 and 4 were added to the blend and mixing was continued for 5 minutes. The mixture was used to prepare 500 tablets on the Stokes B2 rotary machine using 7/16 inch dies and punches. The average weight of the tablets was 607 mg and the hardness was 4 kg. The release rate was determined in the usual manner and gave the following results:

| Time | Release rate, % |
|---|---|
| 1st hour | 45.2 |
| 2nd hour | 76.5 |
| 3rd hour | 88.7 |
| 6th hour | 100 |

EXAMPLE 8

Isosorbide Dinitrate

Isosorbide dinitrate buccal tablets containing 20 mg/tablet were prepared from untreated Metalose 60SH50 (10 wt-% HP) and the following ingredients:

|   | Ingredients | grams | mg/tablet |
|---|---|---|---|
| 1 | Isosorbide dinitrate, 25% triturate | 80 | 80 |
| 2 | Lactose, anhydrous | 40 | 40 |
| 3 | Hydroxypropylmethylcellulose | 25 | 25 |
| 4 | Stearic acid | 3 | 3 |
| 5 | Syloid 244 | 1 | 1 |

Ingredients 1, 2 and 3 were mixed in a blender for 15 minutes, ingredients 4 and 5 were added to the blend and mixing was continued for an additional 5 minutes. The mixture was used in the preparation of 1000 tablets on a Stokes B2 rotary machine using 9/32 inch dies and punches. The average weight of the tablets was 149 mg. The tablets had the following properties:

| Hardness, kg | 3.7 |
|---|---|
| Friability, % | 0.3 |
| Release rate, % | |
| 15 minutes | 42.7 |
| 30 minutes | 73.8 |
| 45 minutes | 88.7 |
| 60 minutes | 100 |

EXAMPLE 9

Nitroglycerin

Nitroglycerin buccal tablets containing 6.5 mg/tablet were prepared with untreated Metalose 60SH50 (hydroxypropoxyl content 10.3 wt-%) and the following ingredients:

|   | Ingredients | grams | mg/tablet |
|---|---|---|---|
| 1 | Nitroglycerin, 10% in lactose Triturate | 143 | 71.5 |
| 2 | Lactose, anhydrous | 80 | 40 |
| 3 | Hydroxypropylmethylcellulose | 44 | 22 |
| 4 | Sodium carboxymethylcellulose | 44 | 22 |
| 5 | Stearic acid | 6 | 3 |
| 6 | Syloid 244 | 2 | 1 |

The ingredients were mixed in the same manner as described in Example 8 and were compressed into 500 tablets using 9/32 inch dies and punches on a Stokes B2 rotary machine. The average weight of the tablets was 159 mg. The tablets had the following properties:

| Hardness, kg | 2.3 |
|---|---|
| Friability, % | 0.3 |

-continued

| Release rate, % | |
|---|---|
| 15 minutes | 61.4 |
| 30 minutes | 93.8 |
| 45 minutes | 100 |

The foregoing is exemplary and illustrative of compositions and products responding to the present invention, but it is to be understood that they are not limitative since many active ingredients of various types can be employed in the new long-lasting carrier so long as they are absorbable into blood or tissue from the general intestinal tract and other bodily surface and area within and outside the body. The invention is also intended to cover other dosage forms or forms for application of sustained release ingredients such as vaginal and rectal suppositories. The lozenges and tablets particularly act on oral, oropharyngeal intestinal and other regions of the gut. The total dosage is governed by usual medical considerations or physician's directions and when sufficiently large doses of active medicament are incorporated in the unit dosage form, systemic as well as local action is obtained to overcome or control the pathological condition or disorder being treated.

What is claimed is:

1. A carrier base material combined with a therapeutically active medicament and shaped and compressed to a solid unit dosage form having a regular and prolonged release pattern upon administration, the carrier base material being hydroxypropylmethylcellulose or a mixture of hydroxypropylmethylcellulose and up to 30% by weight of the mixture of ethylcellulose and/or up to 30% by weight of the mixture of sodium carboxymethylcellulose, and wherein the hydroxypropylmethylcellulose has a hydroxypropoxyl content of 9–12 weight-% and a number average molecular weight of less than 50,000.

2. A composition according to claim 1 in which the carrier base material consists of a mixture of hydroxypropylmethylcellulose and 0–30% ethylcellulose.

3. A composition according to claim 1 in which the carrier base material consists of a mixture of hydroxypropylmethylcellulose and 0–30% sodium carboxymethylcellulose.

4. A composition according to claim 1 in which the active medicament is an antacid selected from the group consisting of aluminum trisilicate, aluminum hydroxide and cimetidine.

5. A composition according to claim 1 in which the active medicament is an anti-inflammatory selected from the group consisting of phenylbutazone, indomethacin, naproxen, ibuprofen, flurbiprofen, diclofenac, dexamethasone, prednisone and prednisolone.

6. A composition according to claim 1 in which the active medicament is a coronary dilator selected from the group consisting of glyceryl trinitrate, isosorbide dinitrate and pentaerythritol tetranitrate.

7. A composition according to claim 1 in which the active medicament is a peripheral vasodilator selected from the group consisting of naftidrofuryl oxalate, cyclandelate and nicotinic acid.

8. A composition according to claim 1 in which the active medicament is an anti-infective selected from the group consisting of erythromycin stearate, cephalexin, nalidixic acid, tetracycline hydrochloride, ampicillin, flucloxacillin sodium, hexamine mandelate and hexamine hippurate.

9. A composition according to claim 1 in which the active medicament is a psychotropic selected from the group consisting of fluazepam, diazepam, amitryptyline, doxepin, thioridazine, trifluperazine, fluphenazine, piperothiazine, haloperidol, maprotiline hydrochloride, imipramine, desmethylimipramine, lithium carbonate, lithium sulfate and methylphenidate.

10. A composition according to claim 1 in which the active medicament is a central stimulant selected from the group consisting of isoproterenol, amphetamne sulfate and amphetamine hydrochloride.

11. A composition according to claim 1 in which the active medicament is an antihistamine selected from the group consisting of chlorpheniramine, bropheniramine and diphenhydramine.

12. A composition according to claim 1 in which the active medicament is a laxative selected from the group consisting of bisacodyl, magnesium hydroxide and dioctyl sodium sulfosuccinate.

13. A composition according to claim 1 in which the active medicament is a decongestant selected from the group consisting of phenylpropanolamine and pseudoephedrine.

14. A composition according to claim 1 in which the active medicament is a vitamin substance selected from the group consisting of alphatocopherol, thiamine, pyridoxine and ascorbic acid.

15. A composition according to claim 1 in which the active medicament is a gastrointestinal sedative selected from the group consisting of propantheline bromide and metoclorpramide.

16. A composition according to claim 1 in which the active medicament is diphenoxylate, an anti-diarrheal preparation.

17. A composition according to claim 1 in which the active medicament is a cerebral vasodilator selected from the group consisting of soloctidilum, naftidrofuryl oxalate, co-dergocrine mesylate, papaverine and naftidrofuryl oxalate.

18. A composition according to claim 1 in which the active medicament is an anti-anginal preparation selected from the group consisting of isosorbide dinitrate, pentaerythritol tetranitrate, verapamil, nifedepine, diltiazem and glyceryl trinitrate.

19. A composition according to claim 1 in which the active medicament is an antiarrythmic selected from the group consisting of verapamil, nifedepine, diltiazem, disopyramide, bretylium tosylate, quinidine sulfate, quinidine gluconate and procainamide.

20. A composition according to claim 1 in which the active medicament is an antihypertensive selected from the group consisting of guanethidine monosulphate, methyldopa, oxprenolol hydrochloride, captopril, hydralazine and propranolol.

21. A composition according to claim 1 in which the active medicament is ergotamine, a vasoconstrictor used in the treatment of migraine.

22. A composition according to claim 1 in which the active medicament is a substance which influences blood coagulability selected from the group consisting of protamine sulfate and epsilon aminocaproic acid.

23. A composition according to claim 1 in which the active medicament is an analgesic selected from the group consisting of acetaminophen, acetylsalicylic acid, oxycodeinone, morphine, heroin, nalbuphine, butorphanol tartrate, pentazocine hydrochloride, cyclazacine, pethidine, byprenorphine, scopolamine and mefenamic acid.

24. A composition according to claim 1 in which the active medicament is a hypnotic selected from the group consisting of dichloral phenazone, nitrazepam and temazepam.

25. A composition according to claim 1 in which the active medicament is an antinauseant selected from the group consisting of chlorpromazine and promethazine theoclate.

26. A composition according to claim 1 in which the active medicament is an anticonvulsant selected from the group consisting of sodium valproate and phenytoin sodium.

27. A composition according to claim 1 in which the active medicament is a neuromuscular drug such as dantrolene sodium.

28. A composition according to claim 1 in which the active medicament is a hypoglycemic agent selected from the group consisting of diabenase, glucagon, tolbutamide and insulin.

29. A composition according to claim 1 in which the active medicament is a drug used in treating thyroid gland disorders selected from the group consisting of thyroxine, triiodothyronine and propylthiouracil.

30. A composition according to claim 1 in which the active medicament is a diuretic selected from the group consisting of furosemide, chlorthalidone, hydrochlorthiazide, spironolactone and triampterene.

31. A composition according to claim 1 in which the active medicament is the uterine relaxant medicament, ritodrine.

32. A composition according to claim 1 in which the active medicament is an appetite suppressant selected from the group consisting of phentermine, diethylproprion hydrochloride and fenfluramine hydrochloride.

33. A composition according to claim 1 in which the active medicament is an erythropoietic substance selected from the group consisting of folic acid, calcium gluconate and ferrous sulphate.

34. A composition according to claim 1 in which the active medicament is an antiasthmatic drug selected from the group consisting of aminophylline, theophylline, orciprenaline sulphate, terbutaline sulphate and salbutamol.

35. A composition according to claim 1 in which the active medicament is an expectorant selected from the group consisting of carbocisteine and guaiphenesin.

36. A composition according to claim 1 in which the active medicament is a cough suppressant selected from the group consisting of noscapine, codeine phosphate, codeine sulfate, oxycodone, dihydrocodeine tartrate, oxycodeinone and dextromethorphan.

37. A composition according to claim 1 in which the active medicament is an antiuricemic drug selected from the group consisting of allopurinol, probenecid and sulphinpyrazone.

38. A composition according to claim 1 in which the active medicament is an antiseptic selected from the group consisting of cetylpyridinium chloride, tyrothricin and chlorhexidine.

* * * * *